United States Patent [19]

Hegemann

[11] Patent Number: 4,634,421
[45] Date of Patent: Jan. 6, 1987

[54] VALVE FOR INCONTINENT PATIENTS

[75] Inventor: Manfred Hegemann, Nyack, N.Y.

[73] Assignee: Johnson & Johnson Products Inc., New Brunswick, N.J.

[21] Appl. No.: 759,545

[22] Filed: Jul. 26, 1985

[51] Int. Cl.⁴ .............................................. A61M 1/00
[52] U.S. Cl. ..................................... 604/34; 604/227; 604/335; 251/7; 251/9
[58] Field of Search ....................... 251/7, 9; 222/529; 128/1 R, DIG. 25; 604/34, 33, 249, 250, 256, 277, 335, 323

[56] References Cited

U.S. PATENT DOCUMENTS

| | | |
|---|---|---|
| 788,553 | 5/1905 | Nicolaus . |
| 3,279,656 | 10/1966 | Axtell et al. ............................ 251/9 |
| 3,952,726 | 4/1976 | Hennig et al. ...................... 128/1 R |
| 4,114,640 | 9/1978 | Forman ................................. 251/9 |
| 4,154,226 | 5/1979 | Hennig et al. ...................... 128/1 R |
| 4,351,322 | 9/1982 | Prager ................................. 128/1 R |
| 4,381,765 | 5/1983 | Burton ................................. 604/277 |
| 4,474,182 | 10/1984 | Rea ..................................... 128/341 |
| 4,492,575 | 1/1985 | Mabille ................................. 251/7 |

Primary Examiner—C. Fred Rosenbaum
Assistant Examiner—J. L. Kruter
Attorney, Agent, or Firm—Wayne R. Eberhardt

[57] ABSTRACT

A continent ostomy valve comprising a drainage tube which is secured at one end within the stoma of the patient while the other end passes through an orifice in a disk-shaped valve body which includes releasable clamping means for selectively occluding the drainage tube. The outer end of the drainage tube is stored on the face of the valve body under a cover which encloses the valve body and provides a low profile of uniform configuration.

24 Claims, 6 Drawing Figures

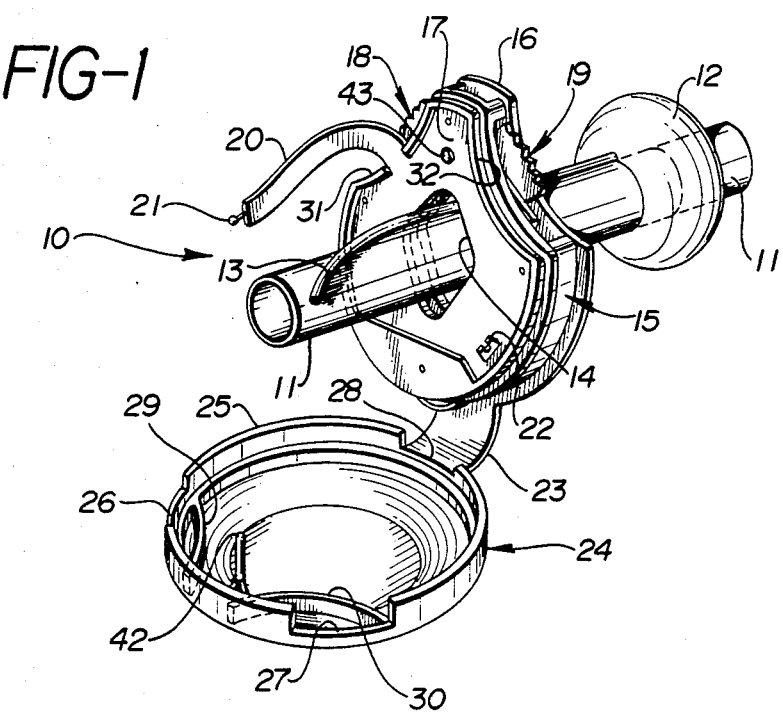
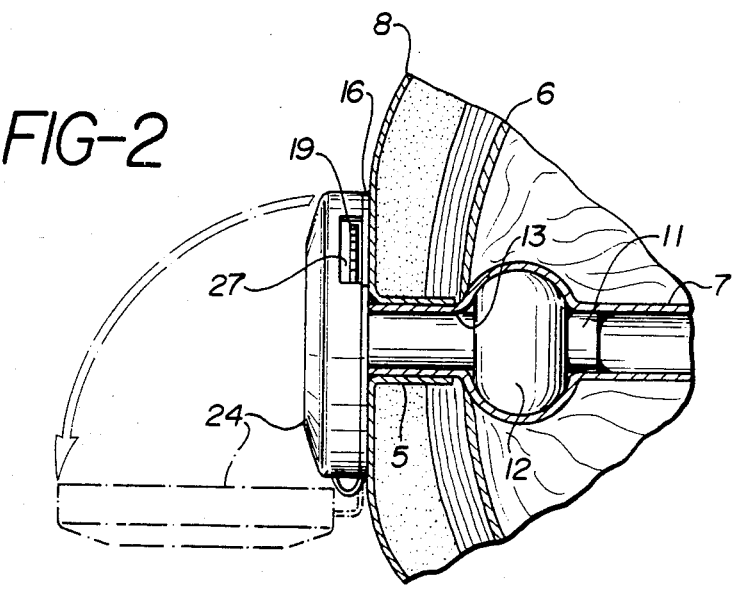

VALVE FOR INCONTINENT PATIENTS

FIELD OF THE INVENTION

This invention relates to the field of medical prosthetic devices, and more particularly, to those devices for use by ileostomy and cholostomy patients to regulate the discharge of body wastes.

BACKGROUND OF THE INVENTION

Bowel diseases and abnormal conditions, including particularly cancer of the lower bowel, have led to surgical operations commonly referred to as ileostomies or cholostomies in which a portion of the bowel is removed and the end of the remaining bowel is brought out through the patient's abdomen. The lower bowel may terminate at the surface of the abdominal skin, or, more commonly, may protrude slightly from the outer skin surface, with the bowel passing through the abdominal fascia, muscle, fat and skin layers. The end portion of the bowel extending to or through the skin is referred to as the stoma. Patients who have had such surgical operations commonly are provided with externally worn containers such as plastic bags, the bags having an opening that is adhesively sealed to the skin about the stoma. A short tube may be anchored at one end within the stoma with its outer end extending outwardly for attachment to a receptacle. The bowel is thus continually open to the flow of its contents through the stoma and into the bag. Such bags must be periodically removed and emptied, of course, and the adhesive seal of the mouth of the bag to the skin surrounding the stoma must be maintained airtight to prevent leakage and escape of odors. If disposable bags are used, means must be found for properly disposing of the bag with their contents. Further, the skin area surrounding the stoma must be maintained very clean, and irritations due to the adhesive seal between the skin and mouth of the bag must be avoided.

Depending largely upon the diet of the patient, the bowel contents issuing from the stoma is characterized by a soupy, water consistency, and the bowel contents may include particles of undigested or partially digested food, all of which must be permitted to escape from the stoma. Thus, it is desirable that the stoma be kept free of obstructions which might interfere with the flow of such bowel contents during periods of discharge.

Continent ostomy devices are devices which occlude the bowel at the stoma for some finite period of time, following which the bowel is emptied and again occluded to repeat the cycle. Patients having a surgically created ileal (Kock) pouch may tolerate occlusion for several hours before the bowel must be emptied. Many types of continent ostomy devices have been suggested for such patients and as an alternative to surgically created biological valves.

U.S. Pat. No. 4,381,765 describes an ileostomy valve which consists of a flexible drainage tube, one end of which is secured within the stoma by means of an inflatable balloon, and the other end of which is retained in a collapsibly folded position on a face-plate outside the stoma to form a leak-proof seal. The valve is opened and the bowel drained by simply releasing and unfolding the exterior end of the drainage tube.

In a preferred embodiment of the continent ostomy valve of U.S. Pat. No. 4,381,765, a wire bail and detachable clamp is utilized to maintain the tube in the folded, sealed configuration. One alternative embodiment utilizes a channel in the outer surface of the face-plate to receive the folded tube with finger like projections extending across the channel to hold the tube in place. Another alternative embodiment uses a hinged gate across the slot to restrain the tube.

An essential feature of the continent ostomy valves of U.S. Pat. No. 4,381,765 is that the valve is closed by folding and collapsing the external portion of the drainage tube. As the tube is released from the folded configuration to drain the bowel, care must be taken to keep the end of the tube pinched shut until ready for drainage to begin.

The physical dexterity required to unfold and refold the drainage tube in order to open and close the valve without inadvertently spilling discharged material has posed a problem for some elderly and physically impaired patients. It is accordingly an object of the present invention to provide an improved continent ostomy valve. It is a further object of the present invention to provide a continent ostomy valve which may be opened and closed with one hand. Is is a further object of the present invention to provide an improved continent ostomy valve having a compact design of low profile. These and other objects will be apparent from the ensuing description and claims.

SUMMARY OF THE INVENTION

The present invention provides a continent ostomy valve having drainage tube closure means incorporated into a low profile valve body associated with a flexible outer end portion of the drainage tube. The complete valve includes a drainage tube having an inner end portion insertable within the stoma of the patient and a flexible outer end portion extending from the stoma. The inner end of the drainage tube includes means for securing the tube within the stoma of the patient.

The outer end of the drainage tube extends through an orifice in low profile valve body which includes releasable tube clamping means acting within the area of the orifice. The drainage tube is effectively opened and closed by activation of the clamping means. The flexible end of the drainage tube extending from the orifice of the valve body is rolled or folded and enclosed by cover means which may be removably secured to the outer surface of the valve body.

DESCRIPTION OF THE DRAWINGS

FIG. 1 is a perspective view of the continent ostomy valve of the present invention with the cover open and the drainage tube extending through the orifice of the valve body.

FIG. 2 is a cross-sectional view of the device of FIG. 1, as secured within the stoma of the patient and with the cover closed.

DESCRIPTION OF PREFERRED EMBODIMENTS

Figure 3:
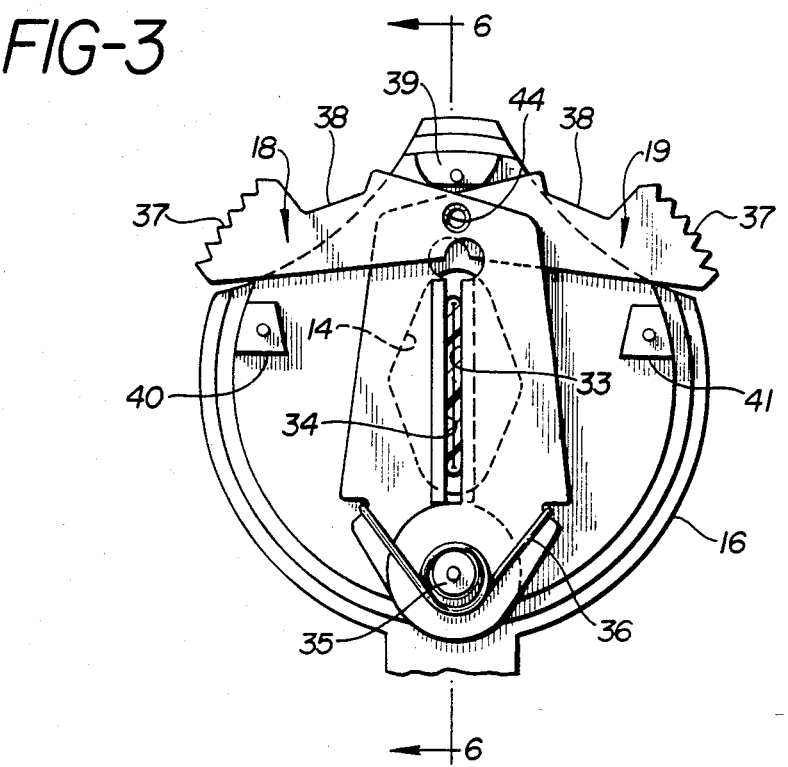
FIG. 3 is a planar view of the valve body partially disassembled to show the tube clamping means in a closed position.

Referring to FIG. 1, the ostomy valve of the present invention designated generally as 10 consists of a flexible drainage tube 11 which is provided with balloon 12 proximal one end thereof and balloon inflation tube 13 extending from the balloon toward the distal end of said drainage tube. Drainage tube 11 and balloon inflation tube 13 extend through central orifice 14 of the valve body indicated generally as 15.

Valve body 15 includes back plate 16, front plate 17 and a pair of tube clamping arms 18 and 19 interposed between said front and back plates, said arms being pivotable between open and closed positions within the area of orifice 14. Specific details of the construction and operation of the valve body and the clamping arms are provided hereinafter.

Valve body 15 includes strap 20 secured at one end near the perimeter of the valve body and terminating at the other end in latch means 21. Cooperating latch means 22 is provided on the valve body at a point across the orifice from the point of attachment of strap 20 whereby strap 20 traverses the orifice of the valve body when secured by said latch means 21 and 22.

Attached to valve body 15 by suitable hinge means 23 is valve cover 24 which includes sidewall 25 so that cover 24 completely encloses the valve body when in a closed position as illustrated in FIG. 2. Side wall 25 of cover 24 optionally have cut out sections 26 and 27 to accommodate the free ends of the tube clamping arms which, in the illustrated embodiment, extend slightly beyond the perimeter of the valve body as hereinafter described in greater detail.

Cover 24 further includes arcuate walls 29 and 30 on the inside surface thereof which, when the cover is positioned over the valve body 15, engage arcuate faces 31 and 32 of the valve body to complete the seal of sidewall 25 around the perimeter of the front plate of the valve body.

Valve body 15 and cover 24 are of low profile so that when cover 24 is in place, as illustrated in FIG. 2, the thickness of the entire assembly is only about 1.0-1.3 centimeters. Moreover, the covered valve body has a smooth outer configuration whereby the device is more readily concealed under the clothing of the patient.

FIG. 2 illustrates the ostomy valve of FIG. 1 in place within the stoma of a patient. With the balloon deflated, the inner balloon end of drainage tube 11 is inserted through stoma opening 5 and into bowel 7 a distance sufficient to place the balloon behind facia layer 6. Balloon 12 is thereupon inflated and the tube withdrawn until the balloon is snug against the facia layer. The outer end of tube 11 is thereupon passed through orifice 14 of valve body 15, as illustrated in FIG. 1, and the valve body snugged down against the surface of skin 8 of the patient, as illustrated in FIG. 2. Clamping arms 18 and 19 are thereupon closed to seal the lumen of the drainage tube and simultaneously hold the valve body in place on the drainage tube. The free end of the drainage tube is folded over and secured under strap 20. Valve cover 24 is then closed to complete the assembly as illustrated.

Figure 4:
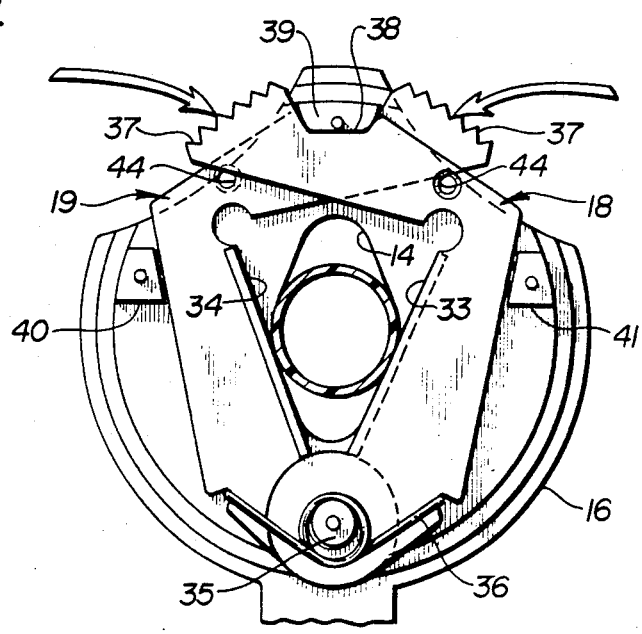
FIG. 4 is a planar view corresponding to FIG. 3 with the tube clamping means in an open position.

The assembly and operation of clamping arms 18 and 19 is most fully illustrated in FIGS. 3 and 4. FIG. 3 illustrates arms 18 and 19 in their closed position effectively clamping tube 11 between faces 33 and 34 respectively to seal the tube. Arms 18 and 19 are mounted on post 35 which forms an axis about which the arms pivot. The arms are biased toward the closed position by the action of coil spring 36.

Clamping arms 18 and 19 are operated by urging the free end 37 of each arm toward the central axis of the valve, as illustrated in FIG. 4. The free end of each arm is provided with an irregular edge surface at 37 to provide a sure, slip-free grip by the thumb and forefinger of one hand of the patient. Each arm is further provided with detents 38 which engage boss 39 on the central axis of back plate 16 to hold arms 18 and 19 in a fully opened position against the bias of spring 36.

Figure 6:
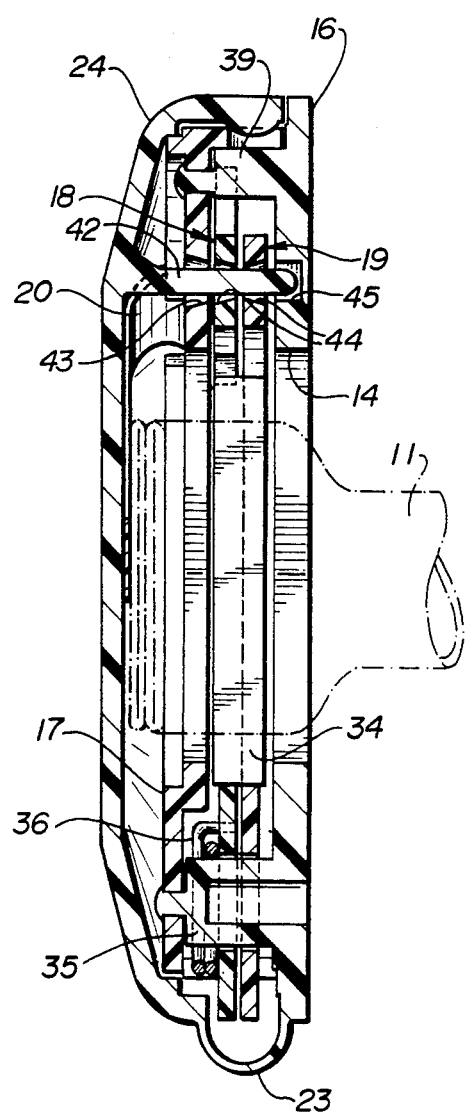
FIG. 6 is a broken away cross-sectional view of the valve body with the cover closed.

Construction details of the valve body are further illustrated in FIG. 6, which is a view in cross-section of the fully assembled valve body through central axis represented by line 6—6 in FIG. 3. FIG. 6 further illustrates the storage of the free end of the drainage tube 11 which lies in a folded configuration under cover 24.

Assembly of the valve body is facilitated by means of spacer blocks 40 and 41 which, together with boss 39 and pivot post 35, provide a four point support to space front plate 17 from back plate 16 a distance sufficient to accommodate clamping arms 18 and 19. Each of said four supports further includes an assembly alignment pin projecting therefrom which mates with alignment holes in front plate 17 during assembly of the unit. The alignment pins of back plate 16 are heat fused to front plate 17 for permanent assembly.

Referring again to FIG. 1, cut outs 26 and 27 in sidewall 25 of cover 24 are sized and positioned to accommodate the free ends of arms 18 and 19, respectively, when the arms are in the closed position as illustrated in FIG. 3. Since the free ends of arms 18 and 19 extend slightly beyond sidewall 25 of cover 24 when the cover is positioned on the valve body, the arms are locked in the closed position until the cover is removed. The position of the free end of arm 19 in cut out 27 may be seen in FIG. 2.

As an optional feature of the ostomy valve there may be included further clamping arm locking and alignment means such as that illustrated in the FIG. 1-6 hereof, wherein cover 24 is provided with locking pin 42 projecting from the inside surface thereof. Front plate 17 is provided with pin receiving aperture 43 as illustrated in FIG. 1, and clamping arms 18 and 19 are each provided with pin receiving apertures 44 which are in axial alignment when the clamping arms are in closed position as illustrated in FIG. 3. Thus, when the clamping arms are closed about tube 11 and cover 24 is closed over the face of the valve, pin 42 extends through the apertures in the front plate and in each clamping arm to align and lock the clamping arms in the closed position. The security of the lock is further enhanced by providing a well 45 in back plate 16 to receive the tip of pin 42 as illustrated in FIG. 6.

Figure 5:
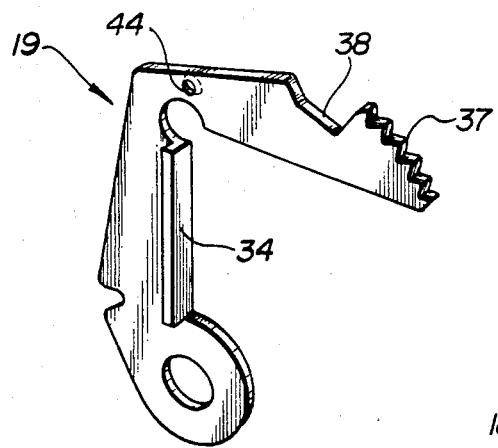
FIG. 5 is a perspective view of one element of the tube clamping means illustrating the construction thereof.

Each of clamping arms 18 and 19 is provided with offset clamping face 33 and 34, respectively, which extend laterally from one surface of the arm over the clamping area as most readily seen in FIG. 5 which illustrates arm 19 in greater detail. Arms 18 and 19 are identical and are assembled so that offset clamping faces 33 and 34 abut when the arms are closed thereby providing a clamping surface of substantial area across the width of the drainage tube. In alternate embodiments not illustrated, the clamping faces may be shaped to provide line contact or angled contact over the area of the clamping surface.

The size of the ostomy valve of the present invention, particularly the diameter of the drainage tube, may be varied to accommodate different patients. Typically, the drainage tube 11 and balloon 12 are made of a physiologically acceptable material such as silicon rubber of the type commonly employed for medical applications. The tube may be on the order of 10 to 15 centimeters in length with an outer diameter of about 13 millimeters and an inner diameter of about 10 millimeters. The inner balloon end of the drainage tube may be rigid or semi-rigid as desired, while the outer end of the tube, which is subject to the action of the clamping arms, must be sufficiently flexible to obtain a gas-tight, water-tight seal when the clamping arms are in the closed position.

The components of the valve body, with the exception of spring means 36, are conveniently fabricated of high density polyethylene or other suitable polymeric material by injection molding. The outer surface of back plate 16, which abuts the skin of the patient, may be provided with cushioning or moisture absorbing means for additional patient comfort. The valve body may have a diameter of from about 4 to 8 centimeters or larger depending on the requirements of the patient, although a diameter of 5 to 6 centimeters is suitable for most applications.

The orifice in the valve body is sized to accommodate the drainage tube in both the open and clamped positions. Preferably, the orifice is elongated on the vertical axis, as illustrated in FIG. 4, and has a maximum width at the horizontal axis whereby the drainage tube remains centrally oriented within the orifice of the valve body while in the open configuration.

While the preceding description has been directed to a preferred embodiment of the present invention, it should be understood that various changes, adaptations and modifications in materials, designs and constructions may be made therein without departing from the spirit and scope of the present invention.

What is claimed:

1. A ostomy valve for incontinent patients comprising a valve body and a drainage tube, said drainage tube having an inner end portion for insertion within the stoma of a patient and a collapsible outer end portion, said valve body associated with said collapsible outer end portion of said tube comprising plate means having an orifice through which said outer end portion of said draining tube passes, releasable clamping means comprising a pair of pivotable clamping arms mounted on said plate means and extending on opposing sides of said orifice for collapsing the lumen of said tube, and removable cover means cooperating with said plate means to define a space enclosing said clamping means and that portion of the outer end of said tube which extends from said clamping means.

2. The valve of claim 1 wherein said releasable clamping means include spring means urging said clamping arms toward a closed position.

3. A for incontienent patients ostomy valve comprising a valve body and a drainage tube, said drainage tube having an inner end portion for insertion within the stoma of a patient and a collapsible outer end portion, said valve body comprising a back plate having an orifice through which said outer end portion of said drainage tube passes, a front plate having an orifice through which said outer end portion of said drainage tube passes, said front plate being spaced from said back plate and secured thereto, releasable clamping means for collapsing the lumen of said tube being mounted between said front and back plates and extending on opposing sides of said orifice, and removable cover means enclosing said front plate and defining a space for storing that portion of the outer end of said tube extending from said front plate.

4. The valve of claim 3 wherein said cover means is attached to said back plate by flexible hinge means.

5. The valve of claim 3 wherein said front plate includes releasable strap means for restraining the outer portion of said flexible tube in a compacted configuration on the face of said front plate.

6. The valve of claim 3 wherein said releasable clamping means include a pair of pivotable clamping arms and spring means urging said clamping arms toward a closed position.

7. The valve of claim 6 wherein each of said clamping arms are pivotedly mounted on a post extending between said front and back plates.

8. The valve of claim 7 wherein said clamping arms are pivotable about a common axis and present opposing clamping surfaces when pivoted to a closed position.

9. The valve of claim 7 wherein the free end of said clamping arms extend beyond the perimeter of said front and back plates.

10. The valve of claim 9 wherein said cover means includes a sidewall with cut outs to accommodate the free ends of said clamping arms when said arms are in a closed position.

11. The valve of claim 7 wherein said back plate includes a boss on the vertical axis between said clamping arms and each of said clamping arms includes an indent to engage said boss when said arms are in an open position.

12. The valve of claim 6 wherein said cover means includes a locking pin projecting from the inside surface thereof, and said front plate and said clamping arms include apertures which are in axial alignment when said clamping arms are in a closed position, said apertures being sized and located to receive said locking pin when said front plate is enclosed by said cover means.

13. The valve of claim 3 wherein the orifice in said front and back plates is configured to have a major dimension at least equal to the dimension of the drainage tube when collapsed by said clamping means and a minor dimension at least equal to the diameter of said drainage tube when not collapsed.

14. A valve body for use with a collapsible tube comprising a back plate having an orifice sized to accept a collapsible tube, a front plate secured to and spaced from said back plate, said front plate having an orifice sized to accept said tube in axial alignment with the orifice in said back plate, clamping means comprising a pair of moveable clamping arms positioned on either side of said orifice between said front and back plates and pivotable about a post extending between said front and back plates, and removable cover means enclosing the front plate of said valve body and defining an enclosed space over said front plate.

15. A valve body of claim 14 wherein said clamping means includes spring means urging said clamping arms toward a closed position.

16. A valve body of claim 14 wherein the free end of each of said clamping arms extends beyond the perimeter of said front and back plates.

17. A valve body of claim 16 wherein said cover means includes a sidewall with cut outs to accommodate the free ends of said clamping arms when said clamping arms are in a closed position.

18. The body of claim 14 wherein said cover means includes a locking pin projecting from the inside surface thereof, and said front plate and said clamping arms include apertures which are in axial alignment when said clamping arms are in a closed position, said apertures being sized and located to receive said locking pin when said front plate is enclosed by said cover means.

19. A valve body of claim 14 wherein said clamping arms are pivotable about a common axis.

20. A valve body of claim 14 wherein said back plate includes a boss on the vertical axis between said clamping arms and each of said clamping arms includes an indent to engage said boss when said arms are in an open position.

21. A valve body of claim 14 wherein each of said clamping arms include a proximal pivot end and a distal free end, and a tube clamping face intermediate said pivot and free ends.

22. A valve body of claim 21 wherein said tube clamping face extends laterally from the plane of said clamping arm in a planar surface.

23. A valve body of claim 14 wherein the orifice in said front and back plates is configured to have a major dimension at least equal to the dimension of said collapsible tube when collapsed by said clamping means and a minor dimension at least equal to the diameter of said tube when not collapsed.

24. A valve body of claim 14 wherein said cover means is secured to said back plate by flexible hinge means.

* * * * *